United States Patent
Krishnaswamy et al.

(10) Patent No.: US 9,254,103 B2
(45) Date of Patent: Feb. 9, 2016

(54) OPERATIVE MICROSCOPE HAVING DIFFUSE OPTICAL IMAGING SYSTEM WITH TOMOGRAPHIC IMAGE RECONSTRUCTION AND SUPERPOSITION IN FIELD OF VIEW

(75) Inventors: Venkataramanan Krishnaswamy, Lebanon, NH (US); Brian William Pogue, Hanover, NH (US)

(73) Assignee: The Trustees of Dartmouth College, Hanover, NH (US)

(*) Notice: Subject to any disclaimer, the term of this patent is extended or adjusted under 35 U.S.C. 154(b) by 718 days.

(21) Appl. No.: 13/586,558

(22) Filed: Aug. 15, 2012

(65) Prior Publication Data
US 2013/0044185 A1 Feb. 21, 2013

Related U.S. Application Data

(60) Provisional application No. 61/523,779, filed on Aug. 15, 2011.

(51) Int. Cl.
| | |
|---|---|
| H04N 13/00 | (2006.01) |
| A61B 5/00 | (2006.01) |
| A61B 19/00 | (2006.01) |
| G02B 21/36 | (2006.01) |
| H04N 13/02 | (2006.01) |
| A61B 5/1455 | (2006.01) |

(52) U.S. Cl.
CPC ............ *A61B 5/7257* (2013.01); *A61B 5/0042* (2013.01); *A61B 5/0073* (2013.01); *A61B 19/5223* (2013.01); *A61B 5/0071* (2013.01); *A61B 5/14553* (2013.01); *A61B 2019/5293* (2013.01); *G02B 21/365* (2013.01); *H04N 13/0239* (2013.01)

(58) Field of Classification Search
CPC ......................................................... A61B 6/00
USPC ................ 348/45, 79; 600/425; 359/368, 385
See application file for complete search history.

(56) References Cited

U.S. PATENT DOCUMENTS

| | | | | |
|---|---|---|---|---|
| 2009/0221920 A1* | 9/2009 | Boppart et al. | ...... | A61B 5/0066 600/476 |
| 2011/0275932 A1* | 11/2011 | Leblond et al. | ...... | A61B 5/0062 600/425 |

OTHER PUBLICATIONS

D'Andrea, et al. "Fast 3D Optical Reconstruction in Turbid Media Using Spatially Modulated Light," Biomedical Optics Express, vol. 1, No. 2, Sep. 1, 2010, pp. 471-481.
Bassi, et al. "Spatial Shift of Spatially Modulated Light Projected on Turbid Media<" J Opt Soc Am A Opt Image Sci Vis, 25(11), Nov. 2008, pp. 2833-2839.
Gioux, et al. "Three-Dimensional Surface Profile Intensity Correction for Spatially Modulated Imaging," Journal of Biomedical Optics, 14(3) May/Jun. 2009, pp. 034045-1-034045-11.

* cited by examiner

*Primary Examiner* — Jefferey Harold
*Assistant Examiner* — Omer Khalid
(74) *Attorney, Agent, or Firm* — Lathrop & Gage LLP

(57) ABSTRACT

An imaging system has a microscope having an objective lens and a projection device configured to project spatially modulated light in one of several preselected predetermined pattern through the objective lens and onto tissue. The system camera configured to record an image of the tissue through the microscope and objective lens as illuminated by the spatially modulated light, and an image processor having a memory with a routine for performing spatial Fourier analysis on the image of the tissue to recover spatial frequencies. The image processor also constructs a three dimensional model of the tissue, and performs fitting of at least absorbance and scattering parameters of voxels of the model to match the recovered spatial frequencies. The processor then displays tomographic slices of the three dimensional model.

21 Claims, 3 Drawing Sheets

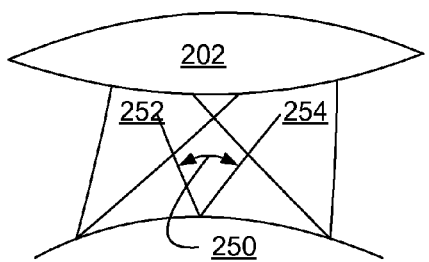
FIG. 3
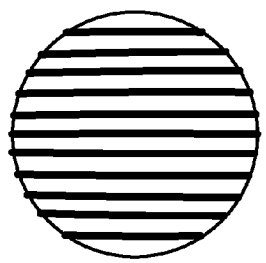
FIG. 4
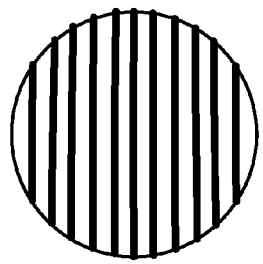
FIG. 5
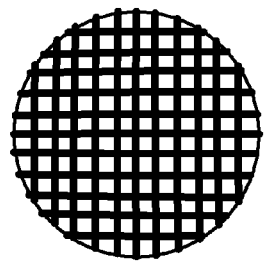
FIG. 6
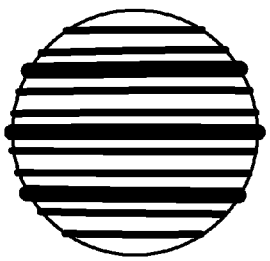
FIG. 7
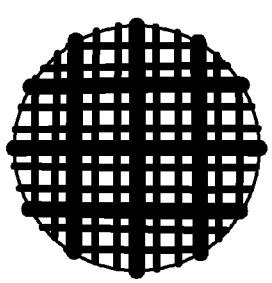
FIG. 8
FIG. 9

OPERATIVE MICROSCOPE HAVING DIFFUSE OPTICAL IMAGING SYSTEM WITH TOMOGRAPHIC IMAGE RECONSTRUCTION AND SUPERPOSITION IN FIELD OF VIEW

RELATED APPLICATION

This application claim priority to U.S. Patent Application Ser. No. 61/523,779 filed Aug. 15, 2011, the disclosure of which is incorporated herein by reference.

FIELD

The present document relates to the field of apparatus for visualizing subsurface features in turbid media; in particular the document describes an enhanced surgical microscope for visualizing subsurface features in brain, breast, and other tissues.

BACKGROUND

While surface features are readily seen when a surgeon views human or other mammalian tissue, whether through a microscope or with the unaided eye, subsurface features may be hidden. Locating and understanding subsurface features may, however, be important for treatment and operative decisions. While light of some wavelengths can penetrate much mammalian tissue, including human brain and breast tissue, to a greater depth than that at which features are readily discernible, the tissue is turbid, scattering the light such that subsurface features may not be easily seen.

There are other fields, from meat inspection and navigation of vehicles through fog, to noninvasive testing of plastic parts including composite aircraft parts, where improved visualization of subsurface features in turbid material may also be of use.

A mammalian, including human, brain 100 typically has a network of blood vessels 102 on the brain surface 104. Generally, brains have a network of fissures 106, known as sulci, and are covered by membranes 108, known as the meninges and including the dura-mater. Beneath the brain surface 104 is typically a layer of grey matter 110, often containing cell bodies of neurons with supporting glia cells, over white matter 112, containing interconnect nerve axons. The brain includes many nerve tracts and nuclei 114 that have particular functions, including the substantia nigra, corticopontine tracts, and many others.

All too many brains may have a tumor 116, cystercerci, or foreign objects for which surgical removal may be desirable. Tumors, especially malignant tumors, also often have invasive processes 118 that can penetrate white and/or grey matter for a considerable distance from the main body of the tumor 116. Brains may also have fluid-filled cavities 120, such as ventricles. Some of these structures have color, turbidity, or other optical characteristics, that differ from other surrounding tissues.

The gray-white matter boundary, tumors 116, processes 118, cavities 120, cystercerci, nerve tracts, and nuclei are inhomogeneities within the brain—regions that have one or more absorbance or scattering parameters that differ from other regions within the brain.

Even after opening of the meninges 108, only brain surface 104, sulci 106, and surface blood vessels 102 may be visible to the unaided eye.

When a tumor 116 is removed, high quality surgery involves removing as much of tumor 116 body and processes 118 as possible, while avoiding removal of excessive normal white or gray matter, and avoiding excessive, unwanted, or unintended collateral damage to underlying structures such as nerve tracts and nuclei 114. A system providing enhanced visibility of subsurface features, including tumor 116 body, tumor processes 118, tracts and nuclei 114, without exposing surgeons and other operative personnel to x-ray radiation, may improve surgical quality.

Andrea Bassi, et al., Spatial shift of spatially modulated light projected on turbid media, *Opt Soc Am A Opt Image Sci Vis.* 2008 November; 25(11): 2833-2839, have proposed that processing images of tissues when illuminated by structured, or spatially modulated, light can be of use in determining the absorption ($\mu_a$) and the reduced scattering ($\mu'_s$) coefficients for diagnostic applications. In this article, Andrea fails to describe incorporation of imaging under structured light into a surgical microscope, and fails to describe using such processing in real time during surgery.

"Structured light" generally refers to light patterns exhibiting some type of periodicity over the field of view.

SUMMARY

An imaging system has a surgical microscope having an objective lens and a projection device configured to project spatially modulated light in one of several preselected predetermined pattern through an objective lens and onto tissue. The system has a camera configured to record an image of the tissue through the microscope and an objective lens as illuminated by the spatially modulated light, and an image processor having a memory with a routine for performing spatial Fourier analysis on the image of the tissue to recover spatial frequencies. The image processor also constructs a three dimensional model of the tissue, and performs fitting of at least absorbance and scattering parameters of voxels of the model to match the recovered spatial frequencies. The processor then displays tomographic slices of the three dimensional model.

A method of generating tomographic images begins with selecting a sequence of spatial modulation images from a library of predetermined spatially-modulated images. Each image is projected onto the tissue through a surgical microscope. Light scattered in tissue is imaged through the microscope. Images are captured 312 of the light scattered in the tissue, and spatial frequencies from separate modulations in the selected spatial modulation image are separated by a digital image processor using a plane Fourier process. A model of tissue is then constructed, and scattering and absorbance parameters are fitted to the extracted spatial frequencies. Selected tomographic images of scatterers, absorbers, and/or oxygenation are displayed.

BRIEF DESCRIPTION OF THE FIGURES

FIG. 3 illustrates an angle between incident and received scattered light.

FIG. 4 illustrates a projected light pattern having spatial modulation in one axis.

FIG. 5 illustrates a projected light pattern having spatial modulation in an axis perpendicular to that of FIG. 4.

FIG. 6 illustrates a projected light pattern having spatial modulation in two perpendicular axes.

FIG. 7 illustrates a projected light pattern having spatial modulation at two frequencies in one axis.

FIG. 8 illustrates a projected light pattern having spatial modulation at two frequencies in two axes.

FIG. 9 illustrates elements of a finite element model having parameters for scattering and absorbance.

DETAILED DESCRIPTION OF THE EMBODIMENTS

Figure 1:
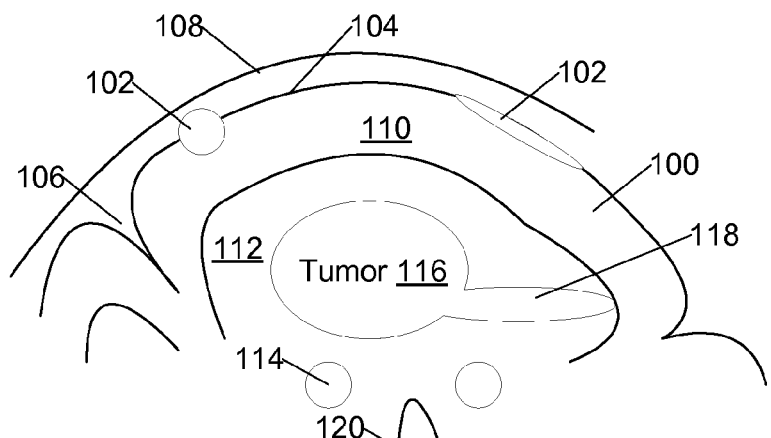
FIG. 1 illustrates a cross section of diseased brain showing blood vessels and tumor.
Figure 2:
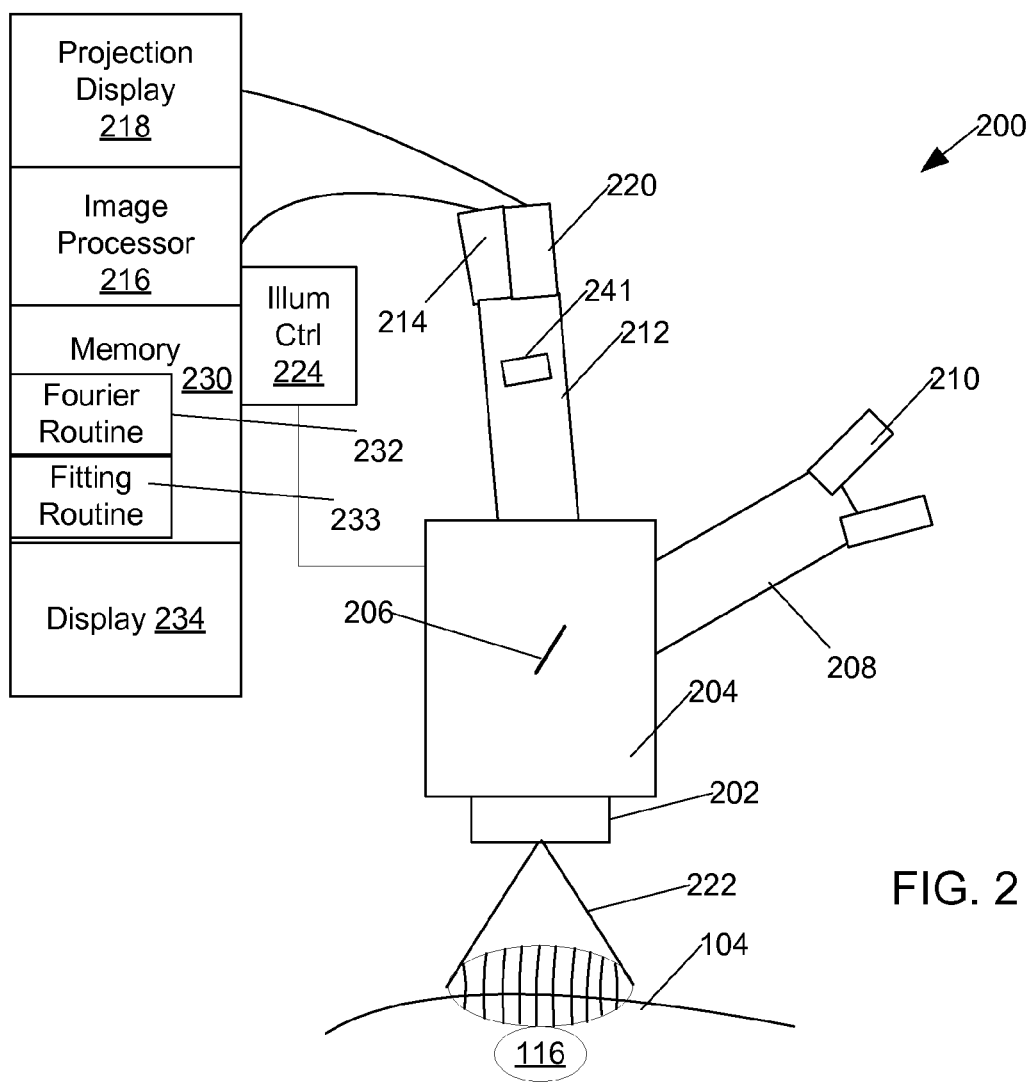
FIG. 2 is a schematic illustration of an optical path of an enhanced surgical microscope.

A surgical microscope system 200 has an objective lens 202 and microscope body 204 with one or more beam-splitters 206. As known in the art of microscopes, beam-splitters 206 serve to send a portion of light received through objective 202 into a first tube 208 and thus into a set of surgeon's eyepieces 210. Similarly beam-splitters 206 serve to allow a second portion of light received through objective 202 to pass into a second tube 212 and thus into an electronic camera 214. In embodiments, beam-splitters 206 may also provide for diverting portions of light received through objective 202 to pass into additional tubes (not shown) to additional eyepieces such as an operative assistant's eyepieces.

In many surgical microscopes, beamsplitter 206 is switchable with a mirror and a tube, thereby permitting an operator to divert received light exclusively into tube 208, or exclusively into tube 212, or diverting a portion of received light into both tubes as herein described.

Images received by electronic camera 214 are transmitted through a cable into an image processor 216. Image processor 216 also controls projection display subsystem 218, that provides structured light and other images to projector 220. Light from projector 220 is coupled through second tube 212 and beam-splitter 206 and emitted through objective 202 as structured light 222 to illuminate brain surface 104. In addition to projector 220, microscope system 200 is equipped with an additional, conventional, illuminator (not shown) as known in the art of surgical microscopes for illumination when the structured light system is not performing tomographic imaging and while the surgeon is operating on brain 104. The conventional illuminator operates under control of illumination control 224, and is adapted to be enabled or disabled by illumination control 224 under command of image processor 216.

Many optical surgical microscopes currently on the market have an illumination system, a microscope body corresponding to body 204, one or a pair of objective lenses corresponding to objective 202, together with first tube 208 and surgeon's eyepieces 210, as well as one or more beamsplitters 206 for diverting a portion of light to one or more accessory ports. The accessory ports typically include one or more ports leading to a second tube 212 or to a third tube and intended for coupling to either an assistant surgeon's eyepieces or a camera; typically they have no provisions for providing or interpreting structured light. In an embodiment the optical surgical microscope is of this type, and both electronic camera 214 and projector 220 are coupled to one or more accessory ports of the surgical microscope. Both light from projector 220 is projected through, and light received by electronic camera 214 is received through, the same objective(s) as light viewed by a surgeon through surgeon's eyepieces 210. The field of view of electronic camera 214 is preferably aligned to be centered within the field of view through surgeon's eyepieces 210.

Image processor 216 has a memory 230 containing machine language instructions 232 for Fourier image reconstruction, and for providing reconstructed tomographic images to a display subsystem 234.

In an embodiment, projector 220 and camera 214 are coupled such that light from the projector 220 does not arrive at the objective 202 colinear with light received through objective 202 and received at camera 214—there is an angle 250 (FIG. 3) between light 252 from the projector 220 incident on the tissue 104 and light 254 received from tissue 104 that is received into camera 214. In an embodiment this angle 250 is accomplished by attaching the projector 220 to microscope tube 212 where one eyepiece of a stereo pair of eyepieces normally would attach, and camera 214 to microscope tube 212 where the second eyepiece of the stereo pair of eyepieces normally would attach.

In an embodiment, the display processor 216 is configured to command the projection display system 218 to configure the projector 220 to provide a sequence of several different predetermined patterns, each pattern of the patterns having a spatial modulation in at least one axis and differing from the other patterns of the sequence of several patterns. In a particular embodiment, the sequence of patterns includes two or more patterns having spatial modulation in the same axis and at two or more different spatial frequencies, and two or more patterns having spatial modulation in a different axis and at the same two or more different spatial frequencies.

In an embodiment, at least one of the illumination patterns provided by the projector is a horizontal bar pattern as illustrated in FIG. 4, this pattern is then alternated with a another pattern having a vertical bar pattern as illustrated in FIG. 5. Typically, these patterns involve not solid vertical or horizontal bars, but shaded bars that produce light having sinusoidal spatial modulation. In various embodiments, patterns having bars at other angles, or axes, such as a 45-degree angle with respect to the vertical, may also be used.

In an enhanced embodiment, at least one of the illumination patterns provided by the projector is a composite as illustrated in FIG. 6 of the horizontal bars of FIG. 4 combined with the vertical bars of FIG. 5. In this embodiment, image processor 216 recovers and separates information retrieved from the horizontal bar pattern from that retrieved from the vertical bar pattern by performing a Fourier techniques such as a Fourier plane filtering operation prior to further image reconstruction. In alternative embodiments having patterns with bars at angles other than vertical and horizontal, the sub-patterns that are combined into each composite pattern are chosen such that separation of information retrieved from each sub-pattern by Fourier techniques is possible.

In particular embodiments, projector 220 is adapted for providing a monochromatic, patterned, incident light. In an embodiment, projector 220 has a digital micromachined mirror array device (DMD) device that patterns monochromatic light incident from a laser. In an alternative embodiment, projector 220 is a high-intensity cathode-ray tube for generating intense bright patterns, light from the tube being passed through an interference filter to select a particular wavelength for illuminating the tissue 104. In another alternative embodiment a liquid-crystal device is used to pattern incident light. In yet another alternative embodiment, an array of light-emitting diodes (LED) directly provides patterned incident light.

In yet another alternative embodiment, an array of light emitting diodes, the array having LEDs organized with two or more colors of LEDs at each pixel location in the array, is provided as a light-emitting element of projection device 220. Embodiments using this multicolor LED array are capable of providing structured light in each of the two or more colors of the LED array separately, or simultaneously. Such color embodiments, if providing structured light in two or more wavelengths simultaneously, may provide structured light with the same, or a different, pattern at each LED wavelength. With these embodiments, a color camera may be used, such color cameras typically have an image sensor having an array of color filters deposited on photosensors organized in groups of four such that each group of four has a filter that will pass each of three primary colors. When a color embodiment having a color camera, not only is it possible to project structured light at each wavelength simultaneously, but to record separate images of scattered light at each wavelength simultaneously.

In an alternative embodiment, a polarizing beam-splitter/combiner 241 is provided in tube 212. Polarizing beam-splitter/combiner 241 polarizes incident light from projector 220 in a first axis while admitting polarized light through beamsplitter 206, objective lens 202, and onto tissue 104. In this embodiment, light received from tissue 104 is admitted through objective lens 202 onto beamsplitter 206, at which a portion is diverted to surgeon's oculars 210 and a portion admitted to polarizing beam-splitter/combiner 241. Light polarized in the same axis as incident light on the tissue is passed to the projector 220, while light having other polarizations is admitted to camera 214. In this embodiment, light specularly reflected from tissue 104 surface retains its polarization and is excluded from camera 214, while light scattered in tissue 104 is admitted to camera 214, thereby reducing interference from specular reflection and enhancing the ability of the system to reconstruct tomographic images of scatterers within tissue 104.

In some embodiments, when a sinusoidal fringe pattern is obliquely projected on a turbid medium, the light will propagate along its incident direction as refracted at tissue 104 surface, and eventually, it will be absorbed and scattered in the tissue. Backscattered light arriving at the surface will be a combination of light diffusively reflected at all depths in the sample and, assuming a linear homogenous medium, it will be modulated at the same spatial frequency of the incident light. Compared to the incident light, received light will, however, be attenuated and spatially displaced.

In an alternative embodiment, the spatially modulated incident light pattern is plane-polarized in a first polarization axis and projected perpendicularly to the tissue surface. In this embodiment, received light is received through a received-light polarizing filter oriented in a second polarization axis perpendicular to the first axis to exclude light reflected from the tissue surface. Since light scattered in tissue beneath the tissue surface loses polarization, the received-light polarizing filter will permit some light scattered in tissue to reach camera 214.

In embodiments, a sequence of patterns having different spatial frequencies are projected by projector 220, as each pattern is projected onto tissue 104, a separate image of received light for each illumination pattern is captured by camera 214 and stored in memory 230.

In alternative embodiments, the sequence of patterns includes patterns having light modulated at two or more specific spatial frequencies in one dimension as illustrated in FIG. 7, or patterns having light modulated at two or more specific spatial frequencies in two dimensions as illustrated in FIG. 8. Once the images for each illumination pattern are stored in memory 230, and the spatial frequencies in both axes are recovered by executing a routine 232 for performing Fourier analysis, a three-dimensional finite element computer model 900 (FEM) of photon migration is constructed, and parameters of the model are then fit to the recovered spatial frequencies. In a particular embodiment, the FEM model has light scattering S and absorbance A parameters at each voxel 902 of the three dimensional model. The model is constrained to have zero scattering S and absorbance A in voxels above tissue surface 104.

The S and A parameters of unconstrained voxels of the FEM model are then fit to the recovered spatial frequencies by a fitting routine 233.

In a particular embodiment, spatially modulated incident light is provided at two, three, or more wavelengths, with spatial frequencies for each wavelength recovered separately. In this embodiment, at least separate absorbance parameters $A_1 \ldots A_N$, and in an alternative embodiment both separate scattering and absorbance parameters, for each wavelength are provided in the model for each voxel. Fitting of the multiple wavelength-specific absorbance parameters $A_1 \ldots A_N$ of the model is done to the recovered spatial frequencies obtained from incident light of the associated wavelengths. Important tissue characteristics such as hemoglobin concentration and oxygen saturation at each voxel may be determined from ratios of the multiple wavelength-specific absorbance parameters determined for that voxel. In various embodiments, additional tissue characteristics such as fat to water ratios and size and density of light-scattering particles may also be determined from the multiple, wavelength-specific, absorbance and scattering parameters determined for that voxel. In an alternative embodiment, the determined hemoglobin concentration, oxygen saturation, fat-to-water ratio, and size and density of light-scattering particles at each voxel is compared to a library of similar parameters determined from normal and abnormal tissue types, and a tissue type is determined for each voxel.

In another embodiment, spatially modulated incident light is provided at an incident wavelength chosen to be a wavelength that is absorbed by a fluorophore found in the tissue. In this embodiment, a filter is positioned between tube 212 and camera 214 that blocks light at the incident wavelength, transmitting light at an emissions wavelength associated with the fluorophore. An image is recorded, and spatial frequencies of emissions are recovered, representing light emitted by the fluorophore. The filter is removed, an image is recorded, and spatial frequencies are recovered, at the incident wavelength, using a low-pass filter to block fluorescence. In this embodiment, initial values for absorbance parameters, scattering parameters, and fluorophore concentration parameters are provided in the model for each voxel, in a particular embodiment absorbance and scattering parameters are assumed constant at both incident and emissions wavelengths. Fitting of the absorbance and scattering parameters is done to the recovered spatial frequencies obtained from incident light, and fitting of the flurophore concentration parameter to the recovered spatial frequencies at the emissions wavelength. In this embodiment, the image processor 216 is capable of displaying a tomographic slice of flurophore concentration as well as slices of absorbance and scattering parameters. In an embodiment, the fluorophore is an endogenous protoporphyrin in the tissue, in an alternative embodiment the fluorophore is protoporphyrin produced in tissue after administration of 5-aminolevulinic acid. In an alternative embodiment, the fluorophore is an injected substance having ability to concentrate in a tumor as known in the art of surgical fluorescence microscopy.

One or more tomographic slices or maps of scattering S or absorbance A, or a composite of the S and A parameters of the fitted model are then displayed by image processor 216 on display 234. Similarly, in an embodiment utilizing patterned incident light at two or more wavelengths, a tomographic map of hemoglobin concentration, or a tomographic map of hemoglobin oxygenation, may also be displayed. In alternative embodiments, a tomographic map of fat-to-water ratio and/or a tomographic map of size and density of light-scattering particles are displayed. In another embodiment, a tomographic map of determined tissue type is displayed.

In an embodiment, camera 214 is adapted to record an image of the brain tissue while the brain tissue is illuminated with spatially unmodulated light, this image being stored in memory 230. In an embodiment this spatially unmodulated light is light from the conventional illuminator of the microscope, in another embodiment this spatially unmodulated light is provided by projector 220. In both embodiments, the image processor 216 is configured with firmware for superimposing a tomographic slice or map of information from the model and as heretofore described upon the image obtained under illumination with spatially unmodulated light, and displaying the resulting composite image.

In an embodiment, information from a selected tomographic slice of the three dimensional model of the brain or other tissue 104, which in some instances may portray tumor 116, is projected at reduced intensity by image processor 216 through projection display 218 and projector 220 onto the brain 104 in a manner such that a surgeon can view the projected tomographic slice through his eyepieces 210 as an image superimposed upon the brain 104. In embodiments, this information may include hemoglobin concentration, hemoglobin oxygen saturation, tissue type, size and density of light-scattering particles, or other determined information for each voxel of the model. The surgeon can use this information, together with information from other sources such as pre-operative MRI images, to operate to remove tumor 116, and processes 118 of tumor, while avoiding other sensitive structures such as tracts 114.

Figure 10:
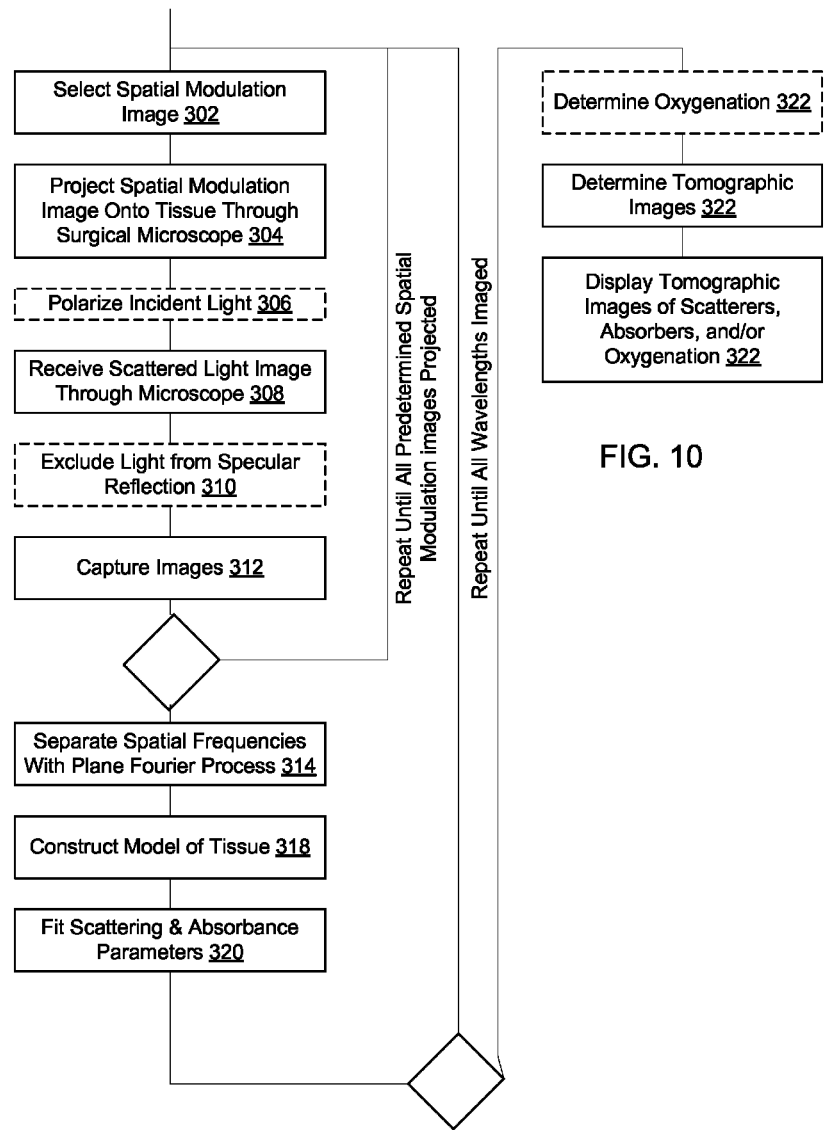
FIG. 10 is a summary flowchart of the method.

The method of generating images is illustrated by the flowchart of FIG. 10. First, a spatial modulation image is selected 302 from a library of predetermined images having spatial modulation in at least one axis. That image is projected onto the tissue through the surgical microscope 304. In some embodiments, the image is projected as incident polarized light 306. Light scattered in the tissue is imaged through the microscope 308, and in some embodiments light from specular reflection is excluded 310 with a polarizing filter. Images are captured 312 of the light scattered in the tissue. The steps of selecting images 302 through separating the spatial frequencies 312 are repeated until all predetermined spatial modulation images have been projected. Spatial frequencies in each captured image resulting from separate modulations in the projected spatial modulation images are separated by a digital image processor with a plane Fourier process 314 or routine, and spatial frequencies are derived for each captured image. A model of tissue 104 is then constructed 318, and scattering and absorbance parameters are fitted to the extracted spatial frequencies 320. The steps of selecting images 302 through fitting the scattering and absorbance parameters are repeated until all wavelengths desired are imaged. The absorbance parameters at each voxel are used to determine oxygenation 322 at those voxels. Desired tomographic images are then determined 322, and selected tomographic images of scatterers, absorbers, and/or oxygenation are displayed 322.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An imaging system comprising:
a surgical microscope comprising at least one objective lens;
a projection device attached to a port of the microscope, the projection device configured to project spatially modulated light in a selected predetermined pattern through the at least one objective lens and onto tissue;
a camera configured to record an image of the tissue as illuminated by the spatially modulated light;
an image processor having a memory with a routine for performing spatial Fourier analysis on the image of the tissue to recover spatial frequencies;
the image processor further comprising a routine for constructing a three dimensional model of the tissue, and a routine performing fitting of at least absorbance and scattering parameters of voxels of the model to match the recovered spatial frequencies; and
apparatus for displaying tomographic slices of the three dimensional model.

2. The imaging system of claim 1 further comprising a beamsplitter configured to permit the camera to receive some light received through the objective lens, and to permit some light received through the objective lens to be presented to an eyepiece.

3. The imaging system of claim 1 wherein the image processor is further configured to present information derived from at least one tomographic slice of the three dimensional model by projecting an image comprising said information through the projector and onto the tissue, where said image may be viewed through an eyepiece of the microscope.

4. The imaging system of claim 1 wherein the image processor is configured to control the projection device to project spatially modulated light in a plurality of preselected patterns, at least one of the preselected patterns having spatial modulation in each of two axes.

5. The imaging system of claim 1 wherein the image processor is configured to control the projection device to project spatially modulated light in a plurality of preselected patterns, at least one of the preselected patterns having spatial modulation at two different frequencies in at least one axis.

6. The imaging system of claim 1 wherein the camera is coupled to record the image, and the projection device configured to project the spatially modulated light through at least one accessory port of the surgical microscope.

7. The imaging system of claim 1 wherein the image processor is configured to display on the apparatus for displaying a tomographic slice of the three dimensional model superimposed on an image recorded by the camera under unmodulated illumination.

8. The imaging system of claim 1 wherein the incident light is polarized in a first state, and wherein apparatus is provided to exclude light polarized in the first state from the camera.

9. The imaging system of claim 8 wherein incident light is polarized by a polarizing beamsplitter in a first state and the same beam splitter is used to exclude light polarized in the first state from the camera.

10. A method of constructing a tomographic image of tissue comprising:
providing a microscope with a digital camera coupled to receive light from an objective of the microscope, and providing the microscope with apparatus for projecting spatially modulated light through the objective of the microscope, projecting spatially modulated light by projecting predetermined images through a surgical microscope onto tissue, imaging light scattered in tissue through the microscope, determining spatial frequencies from separate modulations in projected images and separating these frequencies by a digital image processor using a plane Fourier process, modeling light scattering and absorbance in tissue with a computer model having voxels, fitting scattering and absorbance parameters of voxels of the model to the extracted spatial frequencies, and preparing tomographic images of scatterers and absorbers from fitted parameters of the model.

11. The method of claim 10 further comprising projecting spatially modulated light at a second wavelength by projecting predetermined images through a surgical microscope onto tissue, imaging light at the second wavelength as scattered in tissue through the microscope, and determining spatial frequencies from separate modulations in projected images and separating these frequencies by a digital image processor using a plane Fourier process, wherein the step of modeling further comprises modeling at least an oxygenation parameter, and the step of fitting further comprises determining the oxygenation parameter at voxels of the model.

12. The method of claim 10 further comprising of steps of projecting spatially modulated light at a stimulus wavelength by projecting predetermined images through a surgical microscope onto tissue, imaging light scattered in tissue through the microscope and through a filter, the filter blocking light at the stimulus wavelength, and determining spatial frequencies from separate modulations in projected images and separating these frequencies by a digital image processor using a plane Fourier process, wherein the step of modeling further comprises modeling at least fluorophore concentration, and the step of fitting further comprises fitting the fluorophore concentration at voxels of the model.

13. An imaging system comprising:

a surgical microscope comprising at least one objective lens;

a projection device attached to a port of the microscope, the projection device configured to project spatially modulated light in a selected predetermined pattern onto tissue, the spatially modulated light comprising a pattern of alternating light-and-dark bars;

a camera configured to record an image of the tissue as illuminated by the spatially modulated light;

an image processor having a memory with a routine for performing spatial Fourier analysis on the image of the tissue to recover spatial frequencies;

the image processor further comprising a routine for constructing a three dimensional model of the tissue, and a routine performing fitting of at least absorbance and scattering parameters of voxels of the model to match the recovered spatial frequencies; and apparatus for displaying tomographic slices of the three dimensional model.

14. The imaging system of claim 13 wherein the image processor is further configured to present information derived from at least one tomographic slice of the three dimensional model by projecting an image comprising said information through the projector and onto the tissue, where said image may be viewed through an eyepiece of the microscope.

15. The imaging system of claim 13 wherein the image processor is configured to control the projection device to project spatially modulated light in a plurality of preselected patterns, at least one of the preselected patterns having spatial modulation in each of two axes.

16. The imaging system of claim 13 wherein the image processor is configured to control the projection device to project spatially modulated light in a plurality of preselected patterns, at least one of the preselected patterns having spatial modulation at two different frequencies in at least one axis.

17. The imaging system of claim 13 wherein the camera is coupled to record the image, and the projection device configured to project the spatially modulated light through at least one accessory port of the surgical microscope.

18. The imaging system of claim 13 wherein the image processor is configured to display on the apparatus for displaying a tomographic slice of the three dimensional model superimposed on an image recorded by the camera under unmodulated illumination.

19. The imaging system of claim 13 wherein the incident light is polarized in a first state, and wherein apparatus is provided to exclude light polarized in the first state from the camera.

20. The imaging system of claim 19 wherein incident light is polarized by a polarizing beamsplitter in a first state and the same beam splitter is used to exclude light polarized in the first state from the camera.

21. The imaging system of claim 13 wherein the spatially modulated light is modulated as a sum of two sinusoids in at least one axis.

* * * * *